United States Patent [19]

Della Valle et al.

[11] Patent Number: 5,679,667

[45] Date of Patent: *Oct. 21, 1997

[54] AMINOALCOHOLS-N-ACYL DERIVATIVES AS THERAPEUTICAL AGENTS AGAINST THE NEUROGENIC ENDONEURAL EDEMA OF THE PERIPHERAL NERVE

[75] Inventors: Francesco Della Valle; Silvana Lorenzi; Federica Della Valle, all of Padova, Italy

[73] Assignee: Lifegroup S.P.A., Rome, Italy

[ * ] Notice: The term of this patent shall not extend beyond the expiration date of Pat. No. 5,506,224.

[21] Appl. No.: 326,958

[22] Filed: Oct. 21, 1994

Related U.S. Application Data

[63] Continuation-in-part of Ser. No. 45,767, Apr. 14, 1993, abandoned.

[30] Foreign Application Priority Data

Apr. 24, 1992 [IT] Italy ................................ MI92A0979

[51] Int. Cl.$^6$ ................ A61K 31/555; A61K 31/56; A61K 31/44; A61K 31/385; A61K 31/38; A01N 37/12

[52] U.S. Cl. .................. 514/182; 514/354; 514/356; 514/440; 514/448; 514/563; 514/564; 514/567; 514/825; 514/863; 514/885; 514/886; 514/887; 514/903; 514/914; 514/621; 514/625

[58] Field of Search ................ 514/621, 625, 514/182, 356, 440, 448, 563, 564, 567, 825, 863, 885, 886, 887, 903, 914

[56] References Cited

U.S. PATENT DOCUMENTS 5,506,224 4/1996 Della Valle et al. ................ 514/182

OTHER PUBLICATIONS

Cahill, J.I., et al, Neuropathology and Applied Neurobiology 1986, 12, 459–475, "Stringhalt in Horses: A Distal Axonopathy".

Randall, Lowell O., et al, Arch. Int. Pharmacodyn., 1957, CXI, No. 4, 409–419, "A Method for Measurement of Analgesic Activity on Inflamed Tissue".

Chemical Abstracts 85: 56772a (1978).

Chemical Abstracts 83: 604u (1975).

Enerback et al, "Mast Cells in Normal and Sectioned Peripheral Nerve", *Zeitschrift fur Zellforschung*, 66, (1965), pp. 596–608.

Kruger et al, "Mast Cells and Multiple Sclerosis: A Light and Electron Microscopic Study of Mast Cells in Multiple Sclerosis Emphasizing Staining Procedure", *Acta Neurol Scand*, 81, (1990) pp. 31–36.

Toms et al, "Identification of IgE–Positive Cells and Mast Cells in Frozen Sections of Multiple Sclerosis Brains", *Journal of Neuroimmunology*, 30, (1990), pp. 169–177.

Olsson et al, "Recent Applications of Tracer Techniques to Neuropathology, with Particular References to Vascular Permeability and Axonal Flow" *Recent Advances in Neuropathology*, 2, (1979), pp. 1–25.

Olsson et al, "Proliferation of Mast cells in Peripheral Nerves During Wallerian Degeneration", *Acta Neuropath*, (Berlin) 13, (1969), pp. 111–121.

Mellick et al, "Longitudinal Movement of Radioiodinated Albumin within Extravascular Spaces of Peripheral Nerves Following Three Systems of Experimental Trauma", *J. Neurol. Neurosurg. Psychiat.*, 30, (1967), pp. 458–463.

Nennesmo et al, "Mast Cells in Nerve End Neuromas of Mice" *Neuroscience Letters*, 69, (1986), 296–301.

Aloe et al, "Nerve Growth Factor and Distribution of Mast Cells in the Synovium of Adult Rats", *Clinical and Experimental Rheumatology*, 10, (1992), pp. 203–204.

J.C.Foreman, "Neuropeptides and the Pathogenesis of Allergy", *Allergy*, 42, (1987), pp. 1–11.

Aloe, et al, "Mast Cells Increase in Tissues of Neonatal Rats Injected with the Nerve Growth Factor", *Brain Research*, 133, (1977), pp. 358–366.

Olsson, "Mast Cells in the Nervous System", *Int. Rev. Citology*, 26, (1968), pp. 27–70.

Lindholm et al, "Interleukin–1 Regulates Synthesis of Nerve Growth Factor in Non–Neuronal Cells of Rats Sciatic Nerve", *Letter to Nature*, Nature, vol. 330, Dec. 17, (1987), pp. 658–659.

Roe et al, "Fatty Acid Amides. V.[1] Preparation of N–(2–Acetoxyethyl)–amides of Aliphatic Acids", *Journal of American Chemistry Society*, Notes vol. 74, Feb. 22, (1952), pp. 3442–3443.

Heine et al, "Relationships Between Mast Cells and Preterminal Nerve Fibers", *Z. Mikrosk.–Anat. Forsch.*, 89, (1975), pp. 934–937.

Appenzeller et al, "The Nerves to Blood Vessels Supplying Blood to Nerves: The Innervation of Vasa Nervorum", *Brain Research*, 304, (1984), pp. 383–386.

Wehling et al, "Synovial Cytokines Impair the Function of the Sciatic Nerve in Rats: A Possible Element in the Pathophysiology of Radicular Syndromes", *Neuro–Orthopedics*, 7, (1989), pp. 55–59.

*Primary Examiner*—Theodore J. Criares
*Attorney, Agent, or Firm*—Watson Cole Stevens Davis, P.L.L.C.

[57] ABSTRACT

Aminoalcohols N-acyl derivatives useful in the prevention and in the treatment of mammalian pathologies induced by mast cell degranulation in consequence of peripheral nerve noxae.

18 Claims, No Drawings

AMINOALCOHOLS-N-ACYL DERIVATIVES AS THERAPEUTICAL AGENTS AGAINST THE NEUROGENIC ENDONEURAL EDEMA OF THE PERIPHERAL NERVE

RELATED U.S. APPLICATIONS

This application is a continuation-in-part of U.S. application Ser. No. 08/045,767, filed on Apr. 14, 1993, now abandoned, which is herein incorporated by reference.

FIELD OF THE INVENTION

The present invention relates to a therapeutical method for the prevention and the treatment of mammalian pathologies involving a neurogenic endoneural edema induced by mast cell degranulation in consequence of peripheral nerve noxae, comprising the administration of an effective amount of aminoalcohol N-acyl derivatives.

PRIOR ART DISCLOSURE

It is known that noxae of different origin in the peripheral nervous system determine significant alterations both in the neural components and in the microenvironment of the injured nerve.

From a strictly anatomical point of view the peripheral nerve is a complex structure of neural components, namely Schwann cells and axons, and non-neural components, that is connective matrixes, extracellular fluids and blood vessels. The extracellular fluids together with the connective matrixes form the microenvironment, through which the exchanges of the exogenous nutritious substances and endogenous substances produced by the same neural cells (mainly the Schwann cells, because analogous exchanges between the axons and the blood is accomplished through the axoplasmatic flow) occur between the blood and these neural cells.

These two components, e.g. the microenvironment and the neural portion, together form a nervous fasciculus which is structurally separated by the perineurium from the surrounding tissues, so that a tubular structure originates, physically delimited by the perineural barrier functionally comparable with the hematoencephalic barrier. The purpose of this barrier is to regulate the fine homeostasis between the inside (endoneurium) and the outside (epineurium); the perineurium has therefore the function of a quail-quantitative homeostatic regulation of the microenvironment fluids with respect to the external ones.

Another structurally and fundamentally important element for the homeostatic equilibrium maintenance of the microenvironment extracellular fluids consists in "vasa nervorum", the blood vessels through which the blood arrives at the nerves.

The endoneural extracellular fluids are in fact in equilibrium with blood serum, which arrives through these vessels.

Blood vessels are in turn innervated by the free nerve endings of the so called "nerva vasorum". In other words they are intramural terminations innervating the vasa nevorum, having essentially a peptidergic origin. The main peptides contained in these terminations are substance P, bradykinin, VIP and NPY. These terminations also contain conventional neurotransmitters, mainly serotonin and dopamine (Appenzeller O. et al., Brain Res. 1984, 304(2), 383–386).

Under many lesive conditions of the peripheral nerve having traumatic, toxic, dysmetabolic or infective-immune causes, a hyperactivation situation is observed for these nervous endings which release high amounts of the aforementioned neuropeptides, locally active in the area delimited by the epineural barriers. The etiopathogenetic meaning of this nervous hypeperstimulation becomes clear if one recognizes that a narrow microanatomic relationship exists between the nervous peptidergic endings and particular immunocomponent cells, like the mast cells (Heine H. et al., Z. Mikroskop. Anat. Forsch., 1975, 89, 934–937).

In this regard it is important to remember that mast cells are widely present in the peripheral nerve both in the epineurium where they are located along the blood vessels, and in the perineurium where they are also associated with the capillary vessels. Mast cells are also present in the endoneurium, more in the distal portion of the nerve than in the proximal one (Olsson Y., Int. Rev. Citol., 1968, 24, 27–70).

Furthermore it is important to point out that the most recent researches have demonstrated that, in consequence of a lesion of the peripheral nerve, a dramatic increase of RNA messenger for the NGF (nervous growth factor), as well as of the NGF protein synthesis, occurs in neural and non-neural cells (Schwann cells and fibroblast type cells) associated with the nerve involved in the lesion (Lindholm D. et al., Nature, 1987, 330, 658–659). The above mentioned phenomena are regulated by the synthesis of a cytokine, interleukin-1, produced by the activated macrophages (Wehling P. et al., Neuro-orthopedics, 1989, 7, 55–59). This marked increase of NGF in the lesion site determines in its turn a considerable increase of the number of the local mast cells acting as "gate keepers" and therefore it amplifies the morphofunctional phenomena as a consequence of a lesive noxa (Aloe. L., Levi Montalcini R., Brain Res. 1977, 133, 358–366: Aloe L. et al., Clin. Ext. Rheumatol., 1992, 10, 203–204).

Thus the peptidergic nervous fiber-mast cell functional unit is involved in many paraphysiologic events such as pain, neurogenic inflammation and the local regulation of the blood flow (Foreman J. C., Allergy, 1987, 42, 1–11). It is in fact important to remember that the substance P release, induced by nervous stimulation, causes a mast cell hyperactivation condition able to determine degranulation of the preformed mast cell stores of mediators such as histamine, serotonin, tumor necrosis factor (TNF), involved in the induction, amplification of the inflammatory processes and formation of a local edema.

Under many conditions of the peripheral nerve injury caused or associated with inflammatory processes, alterations of the perineurium are observed, but above all very significant changes are noted both in the composition and in the amounts of endoneural fluids with impressive edema conditions which, although generally representing a consequence of the nervous stimulation induced by the injury and therefore not being its primary cause, actually determine a significant worsening of the pathologic situation.

Following the neurogenic edema onset, significant alterations of the vascular permeability, both of the endoneural and of the perineural microvessels take place, thus compromising the protective function of the perineural barrier.

The edema can occur at the level of any nervous compartment; in other words in consequence of a noxa, a fluids accumulation may be observed at the perineural, epineural level or again at the endoneural one.

Besides the anatomic localization, it is important to distinguish between the edema characterized by an alteration of the vasal permeability to proteins with their consequent extravasation, and the edema not having this protein leakage.

Under many conditions of peripheral nerve injury, a consistent pattern of endoneural neurogenic edema take place together with a remarkable protein extravasation as a consequence of the nervous hyperstimulation.

During the neurogenic endoneural edema formation, the first crucial event consists in the perineural barrier nerve/blood breaking, determining a precocious protein leakage wherein, as previously mentioned, mast cell activation and the consequent release of the endogenous neurotransmitters play a key role. Mast cell degranulation, following peripheral nerve traumas with consequent mediators release, such as histamine, can increase the vasal permeability which in the first place is the main cause of the edema formation (Olsson Y., Int Rev. Citol., 1968, 24, 27; Nennesmo I. et al., Nuerosci, Lett. 1986, 69, 296).

Actually the same mediators, successively in association with inflammation specific mediators, after having caused a rapid increase of the endoneural pressure for the edema formation, slow down the vascular permeability, by further increasing the endoneural pressure, thus determining secondary degenerative injuries (Mellick R. S. et al., J. Neurol. Neurosurg. Psychiatry, 1967, 30, 458).

The neurogenic endoneural edema has therefore important implications from a pathogenic point of view under many peripheral, somatic and autonomic neuropathological conditions. In fact, besides slowing down the endoneural microcirculation, therefore blocking the nutritious substances supplied by a mechanical type action to the neural components which, as a consequence of that, lead to death, the edema condition favours, in presence of a high protein concentration deriving from the protein leakage increase, a remarkable production of collagen and of a cultural medium, suitable for the proliferation of fibroblasts, mast cells and Schwann cells, which are able to induce a fibrosis that compromises the nerve functionality.

Therefore, the edema formation at the level of the microenvironment (matrix and extracellular fluids) is associated to other pathologically important alterations, as for example fibroblasts and mast cells proliferation, alterations which may assume a primary pathogenic role.

It is finally important to point out that, following the neurogenic edema formation, a vicious circle starts, where mast cells play a primary role in the induction (first phase of the edema induced by mast cell degranulation) and in the worsening of the edema state (second phase of the edema associated with fibrosis and mast cell proliferation).

In other words, in consequence of a peripheral nerve lesion, an immediate first cellular reaction occurs in the lesion site, identifiable as a degranulation process of the endoneural mast cells followed by a release of mediators which results in an edema formation. As a consequence of the edema condition, a process of cellular proliferation starts, where an important component is again represented by mast cells. In this second phase also distal alterations, with respect to the primary site of lesion, known as Wallerian degeneration, appear at the level of the nerve. Also in the case of the Wallerian degeneration the increase in mast cell proliferation is considerably higher in the endoneural compartment than in the peri- and epineural one, occurring in the distal portion of the nerve (Olsson Y. et al., Acta Neuropath. 1969, 13, 111).

However the edema formation is associated also with an impressive alteration of the perineurium permeability at the lesion site (Olsson Y. et al., Rev. Adv. Neuropathol., 1979, 2, 1). This modification starts very quickly during the first hour from the injury and lasts for some weeks, but it seems to involve only the proximal portion of the lesion and not the distal one and it does not seem to be connected with a protein leakage.

Furthermore the perineurium edema does not seem to be sensitive to the inflammation mediators.

Therefore due to the above mentioned features, from a pathologic point of view, the neurogenic endoneural edema results to be of primary importance in the peripheral nerve pathologies.

According to the pathological pat tern, the peripheral neuropathies in humans and more generally in mammals can be distinguished in two broad cathegories:

a) The mono or focal neuropathies characterized by localized disturbances usually involving a single nerve trunk and therefore implying a local etiopathogenesis such as direct nerve trauma, nerve compression and entrapment. Accordingly, the clinical features accompanying these mononeuropathies are often of abrupt or rapid onset and vary in nature, entity and duration depending on the type, site and severity of the lesion as well as on the type of the nerve affected. Nonetheless, the degree of nerve injury has a profound influence on the quality of the functional recovery of the nerve.

In fact, depending on the type of the nerve lesion and the nerve morphostructural integrity maintenance, a short reversible functional alteration, due to local ischemic and edematous processes, with nerve conduction disturbance, or long lasting alteration accompanied by structural modifications known as Wallerian degeneration with severe sensory or motor disturbances, can be induced.

b) The poly or generalized neuropathies are characterized by bilateral symmetric disturbances of peripheral nerves in which the distal regions of the longest fibers are usually affected first and are typically of toxic, metabolic, hereditary or infective-immune origin. Accordingly, a distal distribution of motor and/or sensory alterations is the most common clinical pattern observed. Furthermore, although the underlying pathophysiological mechanisms are multiple and vary depending on the type and reversibility of the etiological process, most of these neuropathies are associated with Wallerian-like loss of the distal regions of long fibers, with progression to involve more proximal regions.

In spite of the different pattern of PNS involvement between these two types of peripheral neuropathies, the major clinical features are, indipendently of their etiology, reactive edema often associated with distressful pain, as well as chronic nerve inflammation accompanying the nervous tissue damage. In particular the endoneural edema, not only alters the nerve microenvironment, but also causes, via an increase in endoneural fluid pressure and impaired circulation, endoneural ischemia and hypoxia. All such events are well known to jeopardize peripheral nerve function and to contribute to peripheral nerve damage, while the algic symptom is sustained by local inflammatory mediators produced in the damaged nerve. Furthermore, inflammatory processes have also been shown to cause structural and/or functional changes at the level of the dorsal horn of the spinal cord, a phenomenon which contribute. along with processes of neuronal hyperexcitability and excitotoxicity, to the expansion of the nociceptive receptive fields and to hyperalgesia. In addition, these local changes induce an increase in the sensitivity and/or entity of inflammatory responses towards persistent. even sub-threshold, noxious stimuli.

All these aspects are of utmost importance in clinical practice, where patients suffering from chronic inflammatory events are frequently exposed with time to an augmentation in local tissue reactivity towards stimuli normally unable to trigger an inflammatory response. In addition, the inflammatory reactivity tends to worsen with recurrence on the inflammatory episodes. Both the neurogenic inflammation and sensitivity or hyperalgesia are associated and correlated with the occurrence of increased neurotrasmitters, such as neuropeptides and in particular substance P released from the nervous fibers innervating the vasa nervorum, and with the local synthesis of NGF.

In view of the foregoing, agents capable of down-modulating endoneural mast cell activation and consequent endoneural edema are of therapeutic validity in human peripheral neuropathic conditions, particularly those of traumatic, toxic, dismetabolic or infective-immune etiology.

However attempts to control endoneural mast cell activation and edema have encountered difficulties. The underlying reasons include:

i) lack of knowledge of the mechanisms controlling mast cell activation in endoneural sites;

ii) lack of drugs capable of specifically reducing mast cell activation in endoneural sites. Cromolyn, the only well-known agent capable of specifically inhibiting mast cell activation, is effective upon local administration. In fact its use is essentially topical (e.g. in allergy conditions);

iii) availability of only non-specifically targeted drugs (e.g. steroidal and non-steroidal anti-inflammatory drugs) whose unwanted or serious collateral side-effects do not warrant their use in many peripheral nerve diseases.

Quite recently the Applicant has found compounds active in modulating mast cell degranulation processes, acting with a local antagonist auracoid type mechanism of action, and which can be advantageously used in the treatment of autoimmune pathologies, as described in the U.S. copending patent application Set. No. 08/148,557.

It is in fact known that, in autoimmune diseases, pathologic autoaggressive phoenomena occur, revealing themselves through processes of localized tissue damage where specific immunocompetent cells, and among them mast cells, play a central etiopathogenetic role.

The mast cells are in fact a cellular population residing in tissues which, self activating in situ, proceed to predetermine the biologic sequence of the inflammation, releasing several neurotransmitters, often characterized by a considerable cytotoxicity, and are responsible for the localized tissue damage.

Anyway it is known that the mast cell activity is regulated by stimulating neuromediated and immunomediated systems showing an agonist action towards degranulation, and counterbalanced by antagonist and degranulation inhibitory systems, namely mechanisms intervening in general and in local circuits, as for example corticosteroid hormones.

The Applicant has found that the compounds derived from the N-acylation of aminoalcohols such as mono and diethanolamine, can act on mast cells as antagonist local systems through an autacoid type mechanism and, as a consequence of that, they can be advantageously used in the therapy of autoimmune pathologies.

Also N-(2-hydroxyethyl)hexadecanamide, or N-palmitoylethanolamide (N-PEA), belongs to this class of compounds. The activity of this compound was casually discovered in the Fifties, in consequence of the identification of a generic cytoprotective activity of the lipidic excipient, in which this compound was present, of an antirheumatic drug.

The pharmacologic profile of this compound was then studied in experimental patterns by following damages caused by different agents; the interesting ability in increasing the resistance of the animals to various bacterial toxins was deemed the most suitable for the successive pharmaceutical development of this compound. In fact it is on this base that a pharmaceutical product in the form of tablets was launched in Czechoslovakia, whose therapeutical indication was the prevention of the respiratory tract infections.

With respect to what is already known, the Applicant has in fact found that the activity of N-PEA and of the broad class of aminoalcohols N-acyl derivatives described in the above cited copending U.S. patent application is not only directed to a generic and moderate cytoprotective activity, as suggested by the prior art for N-PEA, but on the contrary said class exhibit a specific and important role in the inhibitory modulation of mast cell degranulation and therefore in inhibiting the autoaggressive effects of the autoimmune pathologies. This is the consequence of the inhibition of the uncontrolled release of preformed mast cell granules, containing numerous proinflammatory mediators and in particular preformed granules containing the Tumor Necrosis Factor, a highly cytotoxic cytokine involved in the autoaggressive autoimmune process (Toms R. et al., J. Neuroimmunology, 1990, 30, p. 169–177; Kruger P. G. et al., Acta Neurol. Scand., 1990, 81, p.331–336).

What is described in the above mentioned copending U.S. patent application does not imply an involvement of these compounds in the treatment of the neurogenic endoneural edema under peripheral nerve damage conditions, since the endoneural compartment results to be effectively protected by the barrier formed by the perineurium, whose function was previously described. Therefore it does not result as an obvious consequence the ability of the same compounds in blocking endoneural mast cell degranulation, induced by a nervous hyperstimulation on lesive base of the peripheral nerve.

SUMMARY OF THE INVENTION

The Applicant has now found that the degranulation and the consequent mast cell proliferation occurring in consequence of traumatic, toxic, dysmetabolic or infective-immune noxae of the peripheral nerve, can be effectively antagonized by administering an aminoalcohol N-acyl derivative of the formula (I):

wherein:

$R_2$ is a residue selected from a $C_1$–$C_{20}$ linear or branched alkylene-hydroxy, optionally substituted in the alkylene chain with at least one aryl group of from 6 to 20 carbon atoms, and a hydroxyarylene of from 6 to 20 carbon atoms optionally substituted in the aromatic ring with at least one alkyl group of from 1 to 20 carbon atoms:

$R_3$ is the same as $R_2$ or hydrogen;

$R_1CO$— is an acyl radical of a monocarboxylic acid belonging to one of the following classes:

a) a linear or branched aliphatic acid of from 2 to 20 carbon atoms, optionally containing at least one ethylenic unsaturation:

b) a linear or branched aliphatic acid of from 1 to 20 carbon atoms, optionally having at least one ethylenic unsaturation, and always having from one to two substituents selected from the group consisting of: OH; $NH_2$; $R_4$—CO, wherein $R_4$ is a $C_1$-$C_{10}$ alkyl; an aryl group of from 6 to 20 carbon atoms, a heterocyclic group consisting of a ring of from 5 to 6 atoms and containing as the heteroatoms from 1 to 2N or S atoms; a cycloalkenyl group of from 5 to 6 carbon atoms containing at least one $C_1$-$C_{10}$ alkyl group;

c) an aromatic acid of from 6 to 20 carbon atoms, optionally substituted in the aromatic ring with at least one substituent selected from the group consisting of: OH, $NH_2$, $OCOR_4$, $OR_4$, wherein $R_4$ has the above mentioned meanings. and $SO_3H$;

d) an aromatic heterocyclic acid, whose ring consists of from 5 to 6 atoms containing as the heteroatoms from 1 to 2 N or S atoms;

e) a biliar acid.

The aminoalcohol N-acyl derivatives of formula (I) are able to control the neurogenic endoneural edema, associated with pathologic states of the peripheral nerve.

Therefore the present invention relates to a therapeutic method for the prevention and the treatment of pathologies of the peripheral nerve having traumatic, toxic, dysmetabolic or infective-immune origin, characterized or associated with neurogenic endoneural edema, comprising the administration by topic or systemic route of an effective amount of the compounds of formula (I).

DETAILED DESCRIPTION OF THE INVENTION

The features and advantages of the aminoalcohols N-acyl derivatives useful in the prevention and the treatment of pathologies of the peripheral nerve system, characterized by a neurogenic endoneural edema according to the present invention, will be better understood in the course of the present detailed description.

The Applicant has surprisingly found that the activity of N-PEA and of the other aminoalcohol N-acyl derivatives of formula (I) is not limited to a generic cytoprotective activity, as suggested by the prior art, but that these compounds, being able to modulate also mast cell degranulation in this specific and protected neurogenic endoneural compartment, play a specific and important role in controlling the neurogenic and endoneural edema in this compartment of the peripheral nerve.

The capability of said aminoalcohol N-acyl derivatives to down modulate endoneural mast cell activation represents a significant breakthrough not only in neurological research but, most importantly, in the prevention and therapy of a well defined aggravating factor, i.e. endoneural edema, in different mammalian peripheral neuropathies.

The action of the aminoalcohol N-acyl derivatives according to the present invention at the level of endoneural mast cells of the peripheral nerve is not evident on the basis of what is already known or previously discovered by the same Applicant, as described in the above mentioned copending U.S. patent application Ser. No. 08/148,557, that is that these compounds can act as local antagonist autacoids.

This therapeutical action is more and more important if we consider that, in consequence of a primary effect in inhibiting mast cell degranulation, these compounds are not only able to prevent the endoneural edema formation but also to prevent mast cell proliferation, which is the determining event of starting the edema vicious circle being the responsible of the chronicity and the severity of the pathology.

This allows to utilize the substances belonging to said class in pharmaceutical compositions suitable to be administered in man and animal for the treatment of pathologies of the peripheral nerve as a consequence of noxae of different origin (e.g. traumatic, toxic, dysmetabolic or infective-immune).

More generally, as this pharmacological activity is related to mast cell degranulation modulation mechanism, on which the whole class of the aminoalcohols N-acyl derivatives proved active, the same activity can be claimed not only for N-PEA, but for the entire class of the compounds according to the present invention. With reference to formula (I), the preferred residue $R_2$ and/or $R_3$ according to the present invention, for a merely illustrative but not limitative purpose, are those of monoethanolamine, diethanolamine, 2-hydroxy-propylamine, di-(2-hydroxy)-propylamine, which bring to the compounds having the following formulas:

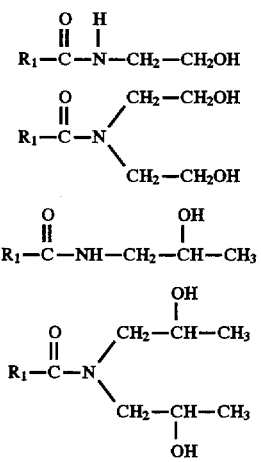

The N-acylderivatives of 2-hydroxy-propylamine and of di-(2-hydroxy)-propylamine may be optically active or a raceme.

For merely illustrative purposes, when $R_1CO$— is an acyl radical of a monocarboxylic acid belonging to class (a), said acid is preferably selected from the group consisting of palmitic, stearic, pentadecanoic, eptadecanoic, lauric, myristic, acetic, butirric, linoleic, valetic, caprylic, valproic, oleic, undecenoic and arachidonic acid.

When $R_1CO$— is an acyl radical of a monocarboxylic acid belonging to class (b), said acid is preferably selected from the group consisting of gamma-hydroxy-butirric, gamma-amino-butirric, lactic, α-lipoic, retinoic, phenyl-hydroxy-acetic, pyruvic and glycholic acid.

When $R_1CO$— is an acyl radical of a monocarboxylic acid belonging to class (c), said acid is preferably selected from the group consisting of salicylic, acetylsalicylic, sulfosalicylic, benzoic, p-aminobenzoic, trimethoxybenzoic and phenylanhranilic acid.

In the case $R_1CO$— is an acyl radical of a monocarboxylic acid belonging to class (d), said acid is preferably selected from the group consisting of nicotinic, isonicotinic and thenoic acid, and when it is an acyl radical of a monocarboxylic acid belonging to class (e), said acid is preferably deoxycholic acid.

We report herewith the following example of preparation of the aminoalcohol N-acyl derivatives according to the present invention for illustrative but not limitative purposes.

EXAMPLE 1

Synthesis of N-palmitoylethanolamide (N-PEA)

Following Roe E. T. et al.'s instructions (J. Am. Chem. Soc., 1952, 74, 3442–3443), the N-palmitoylethanolamide synthesis was accomplished by reacting under reflux ethanolamine and palmitic acid.

Particularly 1 mole of palmitic acid is reacted with 1.5 moles of ethanolamine in ethyl ether for 5–6 hours under nitrogen atmosphere.

The reaction product is then extracted from the reaction mixture and crystallized by using 95% ethanol at 0° C. N-PEA melting point is about 94°–95° C.

The physicochemical properties of N-PEA obtained according to the present example are reported hereinbelow.

| physical state | crystalline powder |
|---|---|
| raw formula | $C_{18}H_{37}NO_2$ |
| molecular weight | 299.48 |
| elemental analysis | C 72.19%; H 12.45%; N 4.68%; O 10.69% |
| solubility in organic solvents | hot methanol. $CHCl_3$, DMSO |
| water solubility | insoluble |
| melting point | 94–95° C. |
| TLC | chloroform/methanol 9:1 Rf = 0.75 |

N-Palmitoyldiethanolamide and the other aminoalcohol N-acyl derivatives according to the present invention are prepared by a similar process, as described in the above mentioned copending U.S. patent application Ser. No. 08/148,557.

i) Biological activity against mast cell degranulation induced by neurogenic stimuli (Substance P)

In order to verify the capability of the aminoalcohol N-acyl derivatives according to the present invention to down-modulate neurogenic mast cell activation under condition of mast cell degranulation induced by mast cell phisiological stimuli, the following biological test was carried out in vivo.

Materials and Methods

Aminoalcohol N-acyl derivatives in question or a physiological solution (DMSO for non water soluble compounds) were administered subcutaneously at the dose of 20 mg/kg in the back of 2-weeks old Sprague Dawley rats, provided by Charles River from Calco, followed 20 minutes later by subcutaneous administration of substance P (1 µl of $10^{-6}$M solution or saline in the ear pinna) able to induce a mast cell degranulation response.

After 30' from the substance P administration the rats were sacrificed and the ear pinna removed for histological assessment of mast cell degranulation by counting the number of degranulated mast cells.

Results

The percentage of degranulated mast cells was considered as a parameter for the biological activity.

It resulted that, whereas substance P induced a degranulation in the majority of mast cells, under pretreatment conditions with the compounds of the present invention a marked inhibition of this phenomenon was observed. The obtained results are reported hereinbelow in Table 1.

TABLE 1 effects of aminoalcohol N-acyl derivatives after subcutaneous administration of 20 mg/kg.

| substance | % of degranulated mast cells |
|---|---|
| solvent | 12 |
| substance P | 92 |
| N-palmitoylethanolamide + subst. P | 65 |
| N-palmitoyldiethanolamide + subst. P | 48 |
| N-palmitoylpropanolamide + subst. P | 49.5 |
| N-stearoylethanolamide + subst. P | 60 |
| N-lauroylethanolamide + subst. P | 54 |
| N-lauroyldiethanolamide + subst. P | 28 |
| N-benzoylethanolamide + subst. P | 48.8 |
| N-benzoyldiethanolamide + subst. P | 36.8 |
| N-oleoyldiethanolamide + subst. P | 44 |
| N-linoleoyldiethanolamide + subst. P | 71 |
| N-salicyloylethanolamide + subst. P | 38 |
| N-(dl-α-lipoyl)-ethanolamide + subst. P | 40 |
| N-pentadecanoylethanolamide + subst. P | 51.1 |
| N-undecanoylethanolamide + subst. P | 34.9 |
| N-acetylsalicyloylethanolamide + subst. P | 54.3 |
| N-desoxycholylethanolamide + subst. P | 58.6 |
| N-butiroylethanolamide + subst. P | 55 |
| N-nicotinoylethanolamide + subst. P | 65.3 |
| N-arachidonoylethanolamide + subst. P | 44.2 | ii) Biological activity against mast cell degranulation of the peripheral nerve

In order to verify the pharmacological activity of aminoalcohol N-acyl derivatives, and in particular of N-PEA, under conditions of traumatic noxa due to crushing of the sciatic nerve and therefore able to induce mast cell degranulation, the following biological test was carried out in vivo as described hereinbelow.

Materials and Methods 10 male Sprague Dawley rats weighing about 200–250 g were divided into two groups and subjected for 15 days to two different treatments: the first group, being the control group, was intraperitoneally treated with a solution of liposomes of soy lecithin, whereas the second group was intraperitoneally treated with 20 mg/kg N-PEA vehiculated on soy lecithin liposomes. The choice of this specific vehicle depended on the poor solubility of N-PEA in aqueous vehicles.

At the $16^{th}$ day the animals were subjected to a bland general anesthesia with ethyl ether, thereby proceeding to the operation of the nerve lesion as hereinbelow described. The left sciatic nerve was exposed just in the spot of its entrance to the haunch, by operating a dissection of the muscular bands. The thus exposed sciatic nerve was then repeatedly compressed as closest as possible to its origin, by using a crushing forceps. The wound was temporarily sewn up and the animals were left to recover.

Three hours after the sciatic nerve compression lesion the animals wereサcrificed in order to take the sciatic nerve sample and to fix it for the histological analysis with a mixture of acetic acid and formalin. The tissues were then cut into fine sections, colored with a mast cell specific dye, 5% toluidine blue in a citrate buffer at pH 4.5, as described by Enerback L. et al. (Zeit. Zellforsch. 1965, 66, 596). The thus prepared tissues were then examined at the optical microscope in order to count mast cells.

Results

With the purpose of evaluating the pharmacologic effects of N-PEA, a comparative analysis of the number of degranulated mast cells of the two rats groups was conducted.

For each animal, a total number of 100 cells in sections in the proximity of the sciatic nerve lesion were examined.

The results are hereinbelow reported:

| Groups | Number of degranulated cells on a total of 100 examined cells |
|---|---|
| CONTROL: | |
| rat No.1 | 43 |
| rat No.2 | 74 |
| rat No.3 | 65 |
| rat No.4 | 68 |
| rat No.5 | 57 |
| average | 61.4 |
| N-PEA 20 mg/kg: | |
| rat No.1 | 35 |
| rat No.2 | 44 |
| rat No.3 | 37 |
| rat No.4 | 25 |
| rat No.5 | 42 |
| average | 36.6 |

As it results from the foregoing, N-PEA is also able to modulate mast cell degranulation processes activated by a traumatic compressive type noxa. In this way it is able to exert a pharmacological effect on neurogenic edema induced by mast cell activation process.

iii) Treatment of horses affected by Stringhalt's syndrome

Stringhalt's syndrome is a neurologic pathology, namely a distal axonopathy specific for peripheral myelinated nerve fibers, characterized by uncontrolled hyperreflection of horse hind legs. In particular, this axonal pathology is presumably of neurotoxic etiology and is associated with both nerve (Wallerian type axonal degeneration) and myelin damage (J. I. Cahill et al., Neuropathology and Applied Neurobiology, 1986, 12: 459–475). No specific therapy, with the exception of treatments with polyvitaminic complexes, is known up to now for this pathology.

Materials and Methods 4 (2 male and 2 female) horses (2–15 years old) are studied, affected by Stringhalt's syndrome with severe neurologic symptomatology (severe hyperreflection and overt gait inability) being present for at least 6 months and the animals being resistant to a polyvitaminic treatment. The horses' characteristics are reported in Table 2.

TABLE 2

Features of the horses subjected to the experimental test.

| Horse | Sex | Age (years) | Disease Period (months) | * | ** |
|---|---|---|---|---|---|
| 1 | m | 2 | 7 | no | no |
| 2 | m | 12 | 6 | yes | no |
| 3 | f | 15 | 10 | yes | no |
| 4 | f | 12 | 6 | no | no |

*Previous different Pharmacologic treatments.
**Contemporaneous different pharmacologic treatments.

The animals are orally treated with 2 g/die N-palmitoylethanolamide for 20 days.

The clinical evaluation is carried out before the treatment ($t_0$), after 10 days ($t_1$), 20 days ($t_2$) and 40 days ($t_3$) of treatment. The neurologic recovery with respect to $t_0$ is evaluated at $t_1$, $t_2$ and $t_3$, and in addition a final observation 1 or 2 months ($t_4$) after the end of the treatment for a more complete evaluation.

Results

The results reported in Table 3 show that, when treated orally with N-palmitoylethanolamide, the animals display an improvement of neurologic deficit of at least 60%.

Such an improvement was still evident following the evaluation of these animals after 1 to 2 months at the end of the treatment.

Some of the treated animals were thereafter reintegrated to the agonistic activity.

TABLE 3 effects on the neurologic recovery determined by evaluating gait ability and hyperreflection, following oral treatment with 2 g/die N-palmitoylethanolamide for 20 days in 4 horses affected by Stringhalt's syndrome.

| Horse | $t_1$ | $t_2$ | $t_3$ |
|---|---|---|---|
| 1 | +20% | +80% | +100% |
| 2 | +30% | +70% | +90% |
| 3 | +10% | +20% | +60% |
| 4 | 0 | +20% | +70% |

Furthermore the functional effects of the pharmacological and clinical activity of N-palmitoylethanolamide (N-PEA) have been verified in experimental model of nerve compression and in clinical conditions of lumbosciatalgia disorder, sustained by a radicular compression of sciatic nerve. In both conditions the painful symptomatology as well as hyperalgesia have been used as functional parameters of evaluation.

vi) Experimental model of sciatic nerve compression in rats

Materials and Methods 20 male Wistar rats weighing 250–300 g each, have been anaesthetized with pentobarbital (50 mg/kg, i.p.).

Sciatic nerve has been exposed at the level of the femoral biceps through an incision of the skin, and has been afterwards separated from the surrounding tissue, avoiding carefully damage caused by compression.

A small polyethylene tube with a longitudinal shape (length 5 mm, internal diameter 0.89 mm) has been subsequently applied on the nerve, avoiding traumatic compression of the nerve itself.

After closing of the incision of muscle and skin, the animal has been recovered from anaesthesia: at the moment of the awakening and during the following days. the movement of the operated paw was observed to be normal and there were no signs of a crushed paw, such as an outwardly turned paw or the dragging of the paw during movement.

In GROUP A, N-palmitoylethanolamide suspended in carboxymethylcellulose has been administered by oral route at the dosage of 10 mg/kg day, 48-24-1 hours before surgery at the sciatic nerve for the application of the tube and afterwards every day for three days. The control group (GROUP B) has been treated in the same way with the vehicle (CMC). The hyperalgesia has been measured with the Randall-Selitto methods (Randall L. O. and Selitto J. J., 1957, Arch. Int. Pharmacodyn., 111, 409–417) at 48 and 96 hours after surgery. All measurements have been performed 20–24 hours after the last pharmacological treatment.

Results

The administration of N-palmitoylethanolamide according to the described protocol is able to counteract the onset of mechanical hyperalgesia both at 48 hours and 96 hours after surgery, as reported in Table 4).

In fact, whereas in the control group (GROUP B) a significant difference has been registered between the operated and non-operated paw in terms of response to mechanical stimulus, in the treated group no differences have been registered neither at 48 hours nor at 96 hours after surgery, between the operated and non-operated paw.

TABLE 4

Mechanical Hyperalgesia after compression of rat sciatic nerve; effect of N-palmitoylethanolamide (10 mg/kg. os) at 48 and 96 hours from the initial compression.

| | 48 hours | | 96 hours | |
|---|---|---|---|---|
| | normal side | operated side | normal side | operated side |
| GROUP A | | | | |
| | 191.1 ± 11.0 | 191.0 ± 12.3 | 211.0 ± 9.5 | 182.0 ± 7.7 |
| GROUP B | | | | |
| | 186.0 ± 5.3 | 144.1 ± 8.2* | 189.0 ± 4.3 | 145.0 ± 6.7* |

The reported values are the average score ± SEM
*p < 0.001 compared to the corresponding normal side, following the test of multiple comparisons of Newman-Keuls.

v) Clinical activity in lumbosciatalgic conditions

Materials and Methods

The efficacy of the compound N-palmitoylethanolamide has been tested in 639 patients with acute and chronic peripheral nerve disorders due to radicular compression for spinal disc protrusion, known as lumbosciatalgia, at the daily dosage of 300 mg (GROUP B) and 600 mg (GROUP C) for 21 days, in comparison with a placebo group (GROUP A).

The age of the patients was comprised between 18 and 75 years. Painful symptomatology has been registered on Visual Analogic Scale (VAS) and the degree above or identical to 5 has been the standard criterion adopted for inclusion of the patients in the trial, together with their diagnosis.

Concomitant diseases or treatments, able to influence in a significant manner the pathology and/or the effect of the compound, as well as the presence of severe pathologies have been taken as criteria of exclusion from the study.

For the evaluation of the therapeutical efficacy, the pain scores on VAS according to Scott Huskinsson, have been monitored during the testing period, from 0 ($t_0$) and after 7, 14 and 21 days of treatment, together with the answers given by the patient and registered by the physician with regard to the single items (24 in total) of the disability questionnaire, items suitable for the evaluation of the functional recovery of the daily activities.

Results

The values of VAS are analyzed as the first parameter of efficacy of the treatment. The average of these values show to be significantly influenced by active treatments. Statistical analysis confirmed the major effect of the active treatments compared to placebo, whereas a significant difference has been seen also among the same active groups. The results obtained at the end of the treatment period are reported in Table 5.

TABLE 5

Visual Analogic Scale Evaluation at basal time at 21$^{st}$ treatment day.

| | Average Scores in mm | | |
|---|---|---|---|
| GROUP | $t_0$ | 21 days | diff. |
| A (placebo) | 65.8 | 46.3 | −27.8% |
| B (300 mg) | 64.7 | 36.1 | −44.2% |
| C (600 mg) | 71.0 | 21.0 | −70.4% |

On the second evaluation parameter used (i.e. disability questionnaire) the registered scores indicate a progress which is summarized in Table 6.

TABLE 6

Disability Questionnaire at basal time and at 21$^{st}$ treatment day.

| | Average Scores | | |
|---|---|---|---|
| GROUP | start | 21 days | diff. |
| A (placebo) | 11.9 | 8.9 | −25.2% |
| B (300 mg) | 1.7 | 6.7 | −42.7% |
| C (600 mg) | 2.7 | 3.5 | −72.4% |

The data reported show the significant decrease of the scores in the group treated with 600 and 300 mg/die of the drug, statistically superior to the slight decrease observed in the patients treated with placebo.

Analyzing the evolution of the objective examinations, it has been seen that some of the parameters of the purely orthopaedic type (articular pain, arthritic pain, functional limitations), as well as a series of more specifically neurologic parameters (deambulation, upright position, passive and active motility, profound reflectivity, pathological reflexes and sensibility) showed clearly statistically significant differences, both between the two treatments versus placebo and between the two treatments themselves, pointing out a dose-dependency that is analogous to the one already reported for the subjective evaluation of pain.

These evidences demonstrate therefore very clearly a pharmacological dose-dependent effect, after administration of the drug, on neurogenic pain which is characteristic for the pathology under study.

The pharmacologic activity of N-PEA, common to the entire class of the aminoalcohols N-acylderivatives whose N-PEA represents the first example, plays a significant role in all the pathologic states of the peripheral nervous system wherein, in consequence of a peripheral nerve noxa both of traumatic type and of toxic, dysmetabolic or infective-immune origin, a sufferance of the nerve occurs, associated with a neurogenic endoneural edema. In practice this is a category of pathologies universally known as peripheral neuropathies, according to a definition given by the World Health Organization (WHO) in WHO-Study group held in Geneva in October 1979, and contained in a Specific Technical Report (Peripheral Neuropathies-Technical Report Series No. 654-WHO 1980). Although the causal agents of peripheral neuropathies are various (varying from chemical agents such as solvents, pesticides, viral or bacterial agents [herpes zoster, HIV, diphtheric toxin], to metabolic causes such as diabetes and uremia and to traumatic causes such as those occurring in intravertebral disc protrusion), as to their classification the World Health Organization divides peripheral neuropathies into four main categories: neuropathies having traumatic, toxic, dysmetabolic and infective-immune origin.

Generally the compounds according to the present invention are parenterally (intravenously, intramuscularly and subcutaneously) or orally administered. In any case under anatomically localized neuropathic conditions such as localized traumatic lesions, topic (dermic, intra- and transdermic) administrations are not to be excluded.

The necessary doses to have therapeutic effectiveness depends on the administration route and on the application modalities, as well as on the pathology severity; furthermore other factors are to be considered connected to the patients' age, body weight and health general conditions. Anyway an acceptable therapeutic range is preferably comprised between 0.1 mg/kg and 50 mg/kg and more preferably between 0.5 and 20 mg/kg.

Relevant undesired side effects of the compounds according to the present invention being unknown, further to a dosage a therapeutic regimen has also to be established based on medical criteria which take into account the acuteness or the chronicity characteristics of the pathology.

Typically the therapeutic regimen may be of from 1 to 2 daily administrations of the drug for 3–4 weeks, even in therapeutic cycles repeated for at least three months. Anyway, under particular acute neuropathic states, short duration regimen are not to be excluded, being characterized by 3–4 daily administrations for 1 or 2 weeks.

Furthermore, as these pathologies are characterized by new acute phases, the aminoalcohol N-acyl derivatives according to the present invention can be advantageously used for a preventive action, as well as for a therapeutic one.

As preventive agents in chronic pathologies characterized by recurrent acute episodes, these compounds can be administered as dietetic integrating components, and the daily dosage foreseen for this specific use of the compounds according to the present invention preferably range from 0.1 to 1 mg/kg, both for human beings and for animals.

The compounds according to the present invention are formulated in pharmaceutical compositions comprising all those substances suitable for the above mentioned administrations and the excipients may be those therapeutically and pharmacologically suitable for the same applications as well as those of a more recent conception able to improve the delivery of these active principles to the site of action.

The preferred formulations for the topical administration (dermic, intra- and trans-dermic) are the buffered solutions, gels, medicated plasters, whereas for the oral systemic administration all the formulations result suitable in the form of dry powder such as granulates, tablets, dragees, soft or hard jelly capsules, containing the compounds dissolved or dispersed in suitable excipients; in the liquid form such as suspensions, aqueous solutions or emulsions wherein these compounds are present even in the form of liposomes, optionally mixed with other lipids; in semisolid form obtained with polysaccharides aqueous suspensions, solutions or emulsions containing the compounds according to the present invention in the form of liposomes optionally mixed with other lipids.

The dietetic integrating components are preferably in the form of dragees, tablets or oily perles.

For the rectal administration, dispersions of the compounds according to the present invention can be utilized in the form of dispersions in an acceptable lipidic excipient.

As to the parenteral administration, the preferred formulations are buffered aqueous solutions or emulsions, containing the compounds of the present invention optionally in the form of simple or mixed liposomes with other biologically acceptable lipids for the parenteral use, or oily solutions; these parenteral formulations can also consist of a lyophilized product readily dispersable in the solvent at the moment of the administration.

The following examples of preferred pharmaceutical compositions are reported for illustrative but not limitative purposes.

Example 1: Tablets

Every tablet contains
| | |
|---|---|
| N-palmitoylethanolamide | 300 mg |
| lactose | 35 mg |
| maize starch | 90 mg |
| polyethylene glycol | 5 mg |
| carboxymethyl cellulose | 15 mg |
| magnesium stearate | 5 mg |
| yellow iron oxyde (E172) | 0.2 mg |

Example 2: Soft Jelly Perles

Every perle contains:
| | |
|---|---|
| N-palmitoylethanolamide | 100 mg |
| soy lecithin | 40 mg |
| peanut oil | 100 mg |
| gelatin | 52 mg |
| glycerol | 16 mg |
| erythrosin (E127) | 0.1 mg |

Example 3: Chewable Jelly Drops

Every drops contains:
Mixed liposomes obtained by sonication and containing:
| | |
|---|---|
| N-palmitoylethanolamide | 200 mg |
| soy lecithin | 100 mg |
| p-hydroxybenzoate | 2 mg |
| purified carrageenin | 40 mg |
| demineralized water | 1.66 g |

Example 4: Syrup 100 g of syrup contain:
Mixed liposomes obtained by sonications and containing:
| | |
|---|---|
| N-palmitoylethanolamide | 2 g |
| soy lecithin | 1 g |
| methyl p-hydroxybenzoate | 0.1 g |
| glycerin | 1.7 g |
| vanilla tincture | 0.15 g |
| orange tincture | 0.6 g |
| saccharose | 19 g |
| demineralized water | q.s. to 100.0 g |

Example 5: Suppository

Every suppository contains:
| | |
|---|---|
| N-palmitoylethanolamide | 30 g |
| soy lecithin | 50 mg |
| triglycerides of fatty acids | q.s. to 1.5 g |

Example 6: Vials

Every vial contains:
| | |
|---|---|
| N-palmitoylethanolamide | 30 mg |
| soy lecithin | 100 mg |
| phosphate buffer pH 7.6 | 2 ml |

Example 7: Vials

Every vial contains:
| | |
|---|---|
| N-palmitoylethanolamide under liposomes form obtained by sonications | 150 mg |
| mannitol | 15 mg |
| bidistilled apyrogen buffered water | q.s. to 1.5 ml |

Example 8: Lyophilized Tiny Bottle

Every lyophilized tiny bottle contains:
| | |
|---|---|
| N-palmitoylethanolamide | 500 mg |
| mannitol | 30 mg |
| glycocoll | 100 mg |

Every vial contains:
| | |
|---|---|
| bidistilled apyrogen buffered water | 2.0 ml |

Example 9: Dermatologic Cream 100 g of cream contain:
| | |
|---|---|
| N-palmitoylethanolamide | 50 mg |
| sorbitan monostearate | 500 mg |
| polyoxyethylen sorbitate | 4.5 g |
| ethanol | 3 g |
| stearic acid | 3 g |
| paraffin oil | 10 g |
| 70% sorbitol | 6 g |
| p-oxybenzoic acid methyl ester | 0.2 g |

-continued

| | |
|---|---|
| p-oxybenzoic acid propyl ester | 0.05 g |
| water | q.s. to 100 g |

Example 10: Dietetic integrating component in jelly perles

Every perle contains:
| | |
|---|---|
| N-palmitoylethanolamide | 30 mg |
| lecithin | 90 mg |
| maize oil | 240 mg |

The pharmaceutical compositions containing as the active principles the compounds according to the present invention may find a valid therapeutic and preventive application in all the mammalian pathologies characterized by an injury of the peripheral nerve associated with a neurogenic endoneural edema substained by mast cell hyperactivation.

In particular the compounds of the present invention can be advantageously administered in the pathologies of the peripheral nervous system, normally those defined as peripheral somatic and autonomic neuropathies having traumatic-compressive, toxic, dysmetabolic or infective-immune origin.

We claim:

1. A therapeutic method for the prevention and the treatment of mammalian pathologies of the peripheral nerve having traumatic, toxic, dysmetabolic or infective-immune origin, characterized or associated with neurogenic endoneural edema and involving mast cell degranulation, comprising administering to a mammal in need thereof an effective amount of at least an aminoalcohol N-acyl derivative of formula (I):

wherein:

$R_2$ is a residue selected from a $C_1$–$C_{20}$ linear or branched alkylene-hydroxy, optionally substituted in the alkylene chain with at least one aryl group of from 6 to 20 carbon atoms, and a hydroxyarylene of from 6 to 20 carbon atoms optionally substituted in the aromatic ring with at least one alkyl group of from 1 to 20 carbon atoms;

$R_3$ is the same as $R_2$ or hydrogen;

$R_1CO$— is an acyl radical of a monocarboxylic acid belonging to one of the following classes:

a) a linear or branched aliphatic acid of from 2 to 20 carbon atoms, optionally containing at least one ethylenic unsaturation;

b) a linear or branched aliphatic acid of from 1 to 20 carbon atoms, optionally having at least one ethylenic unsaturation and always having from one to two substituents selected from the group consisting of OH; $NH_2$; $R_4$—CO, wherein $R_4$ is a $C_1$–$C_{10}$ alkyl, an aryl group of from 6 to 20 carbon atoms, a heterocyclic group consisting of a ring of from 5 to 6 atoms and containing as the heteroatoms from 1 to 2 N or S atoms; a cycloalkenyl group of from 5 to 6 carbon atoms containing at least one $C_1$–$C_{10}$ alkyl group;

c) an aromatic acid of from 6 to 20 carbon atoms, optionally substituted in the aromatic ring with at least one substituent selected from the group consisting of OH, $NH_2$, $OCOR_4$, $OR_4$, wherein $R_4$ has the above mentioned meanings, $SO_3H$;

d) an aromatic heterocyclic monocarboxylic acid, whose ring consists of from 5 to 6 atoms containing as the heteroatoms from 1 to 2 N or S atoms;

e) a biliar acid.

2. The therapeutic method according to claim 1 wherein said residues $R_2$ and/or $R_3$ are selected from the group consisting of

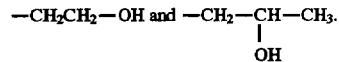

3. The therapeutic method according to claim 1 wherein, when $R_2$ and/or $R_3$ are

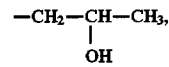

then the N-acyl derivative is optically active or it is a raceme.

4. The therapeutic method according to claim 1 wherein, when $R_1CO$— is an acyl radical of a monocarboxylic acid belonging to class (a), said acid is selected from the group consisting of palmitic, stearic, pentadecanoic, eptadecanoic, lauric, myristic, acetic, butirric, linoleic, valetic, caprylic, valproic, oleic, undecenoic and arachidonic acid.

5. The therapeutic method according to claim 1 wherein, when $R_1CO$— is an acyl radical of a monocarboxylic acid belonging to class (b), said acid is selected from the group consisting of gamma-hydroxy-butirric, gamma-aminobutirric, lactic, α-lipoic, retinoic, phenyl-hydroxy-acetic, pyruvic and glycholic acid.

6. The therapeutic method according to claim 1 wherein, when $R_1CO$— is an acyl radical of a monocarboxylic acid belonging to class (c), said acid is selected from the group consisting of salicylic, acetylsalicylic, sulfosalicylic, benzoic, p-aminobenzoic, trimethoxybenzoic and phenylanthranilic acid.

7. The therapeutic method according to claim 1 wherein, when $R_1CO$— is an acyl radical of a monocarboxylic acid belonging to class (d), said acid is selected from the group consisting of nicotinic, isonicotinic and thenoic acid.

8. The therapeutic method according to claim 1 wherein, when $R_1CO$— is an acyl radical of a monocarboxylic acid belonging to class (e), said acid is deoxycholic acid.

9. The therapeutic method according to claim 1, wherein said aminoalcohol N-acyl derivative of formula (I) is orally administered in the form of dry powder consisting of granulates, tablets, dragees, hard or soft jelly capsules, or in a liquid form consisting of suspensions, aqueous solutions or emulsions wherein the active ingredient is optionally present in the form of liposomes optionally mixed with other lipids, or in semisolid form optionally obtained with polysaccharides aqueous suspension, solutions or emulsions wherein the active ingredient is present in the form of liposomes optionally mixed with other biologically acceptable lipids.

10. The therapeutic method according to claim 1 wherein said aminoalcohol N-acyl derivative of formula (I) is administered as dietetic integrating components in the form of dragees, tablets or oily perles, both for human beings and for animals.

11. The therapeutic method according to claim 1 wherein said aminoalcohol N-acyl derivative of formula (I) is topically, rectally and parenterally administered.

12. The therapeutic method according to claim 11 wherein said aminoalcohol N-acyl derivative is parenterally administered in the form of buffered aqueous emulsions, optionally containing the active ingredient in the form of liposomes optionally mixed with other biologically acceptable lipids, in the form of oily solutions, or in the form of a lyophilized product dispersible in the solvent at the moment of the administration.

13. The therapeutic method according to claim 11 wherein said aminoalcohol N-acyl derivative is rectally administered in the form of dispersions in an acceptable lipidic excipient.

14. The therapeutic method according to claim 11 wherein said aminoalcohol N-acyl derivative is topically administered in the form of buffered solutions, gels or medicated plasters.

15. The therapeutic method according to claim 1 comprising administering daily from once to twice doses of at least an aminoalcohol N-acyl derivative of formula (I) ranging from 0.1 to 50 mg/kg for a period of from 3 to 4 weeks.

16. The therapeutic method according to claim 15 wherein said doses range from 0.5 to 20 mg/kg.

17. The therapeutic method according to claim 15 wherein said aminoalcohol N-acyl derivative is administered for a period of from 1 to 2 weeks.

18. The therapeutic method according to claim 10 wherein said aminoalcohol N-acyl derivative is administered as a dietetic integrating component at daily doses ranging from 0.1 to 1 mg/kg.

* * * * *